United States Patent [19]

Rubino et al.

[11] 4,112,072

[45] Sep. 5, 1978

[54] RESUSPENDABLE DRIED ANTACIDS

[75] Inventors: Andrew M. Rubino, New Providence; Jack J. Margres, Old Bridge, both of N.J.

[73] Assignee: Armour Pharmaceutical Company, Phoenix, Ariz.

[21] Appl. No.: 423,226

[22] Filed: Dec. 10, 1973

Related U.S. Application Data

[63] Continuation-in-part of Ser. No. 252,816, May 12, 1972, abandoned.

[51] Int. Cl.[2] ..................... A61K 33/12; A61K 33/10; A61K 33/08

[52] U.S. Cl. .................................... 424/155; 424/156; 424/157; 424/158

[58] Field of Search ................ 252/816; 424/155, 156, 424/157, 158

[56] References Cited

U.S. PATENT DOCUMENTS

| | | | |
|---|---|---|---|
| 3,239,416 | 3/1966 | Rubino | 424/156 |
| 3,272,704 | 9/1966 | Beekman | 424/156 |
| 3,452,138 | 6/1969 | Granatek et al. | 424/155 |
| 3,579,634 | 5/1971 | Brown | 424/154 |
| 3,599,150 | 8/1971 | Feinberg | 424/88 |

FOREIGN PATENT DOCUMENTS

| | | | |
|---|---|---|---|
| 45-26,518 | 9/1970 | Japan | 424/157 |

OTHER PUBLICATIONS

The Merck Index, 8th Ed., Merck & Co., Rahway, N. J. (1968) pp. 181, 210, 434, 435, 876 & 877.

*Primary Examiner*—Frederick E. Waddell
*Attorney, Agent, or Firm*—Richard R. Mybeck; C. C. Batz

[57] ABSTRACT

Antacid compositions prepared by drying a wet, compressed aluminum hydroxide gel to solid form which are capable of being readily resuspended to yield an opaque, aqueous suspension which reflects the properties of the original compressed gel, are produced by codrying a hydrous, gelatinous aluminum hydroxide material with a di- or trihydroxy alcohol.

18 Claims, No Drawings

RESUSPENDABLE DRIED ANTACIDS

This Application is a continuation-in-part of our copending Patent application Ser. No. 252,816, filed on May 12, 1972, now abandoned.

This invention relates to antacid compositions and more particularly to antacid compositions which are capable of being readily resuspended to yield an opaque, aqueous suspension which reflects the properties of the original wet, compressed aluminum hydroxide gel from which it was formed.

BACKGROUND OF THE INVENTION

Aluminum hydroxide gel is a standard therapeutic for the treatment of peptic ulcer and other symptoms of gastric hyperacidity. Liquid aluminum hydroxide gel closely approaches the ideal for an antacid. However, its liquid form makes it inconvenient to use, especially in the case of ambulatory patients. The liquid gel is quite rapid in its action and give a prolonged antacid effect in the optimum pH range. Further, it is not significantly affected in its antacid properties by pepsin and it does not significantly lose its antacid characteristics in aging. The advantages of the dried gel are obvious. Unfortunately, however, aluminum hydroxide gel undergoes undesirable change on drying during its manufacture and still more change in aging of the dried material. In the dry solid form it exhibits a lag in its rate of reaction with stomach acids and does not give a prolonged antacid effect in the optimum pH range. In addition, its antacid properties are severely affected by pepsin and its activity is less than that of the liquid gel.

Heretofore, it has not been possible to convert a gelatinous antacid system to a dry solid form which can then be resuspended to evidence the properties of the precursor wet, compressed gel. By their very nature compressed antacid gels when converted to the dried state yield products which, when dispersed in water at the usual concentration at or about 4% $Al_2O_3$, settle very rapidly because of poor rehydration properties, among other factors. Such gels have been considered to be "irreversible colloids".

OBJECTS OF THE INVENTION

It is an object of this invention to provide an antacid composition prepared by drying a wet compressed aluminum hydroxide gel to solid form, which composition is capable of being readily resuspended to yield an opaque, aqueous suspension which reflects the properties of the original compressed gel. Another object is to produce dried products which can assume gel-like properties when suspended in water and exhibit sufficient rehydration to minimize grittiness or solid-like character, and to demonstrate slow-settling properties and thixotropy. A further object of the invention is to convert wet antacid gels to a condition which will prevent or inhibit the degradation of the gel-like structure in the drying process.

SUMMARY OF THE INVENTION

In accordance with the invention there is provided an antacid composition prepared by drying a wet, compressed aluminum hydroxide gel to solid form, which composition is capable of being readily resuspended to yield an opaque, aqueous suspension which reflects the properties of the original compressed gel. The product in powder or tablet form comprises the codried combination of a hydrous, gelatinous, aluminum hydroxide material selected from the group consisting of (1) basic aluminum bicarbonate-carbonate, (2) basic aluminum bicarbonate-carbonate in combination with magnesium basic carbonate, magnesium hydroxide, or magnesium trisilicate, and (3) mixtures thereof, together with a foodgrade di- or trihydroxy alcohol suitable for oral ingestion. Such aluminum hydroxide material contains at least 0.4 mol of $CO_2$ per mol of $Al_2O_3$. The analysis of the dried product yields a figure in the range of from 30 to 60 percent by weight for the sum of aluminum hydroxide and magnesium hydroxide calculated as $Al_2O_3$ and MgO and shows that there is also present at least 0.2 mol of carbonate calculated as $CO_2$ for each mol of aluminum oxide.

The novel resuspendable dried antacid compositions may be prepared by contacting the wet gels with a suitable di- or trihydroxy alcohol for a short period of time and then spray drying the suspension.

DETAILED DESCRIPTION OF THE INVENTION

Broadly, any available aluminum hydroxide gel can be used in accordance with the present invention provided that the gel is a wet gel which has not been predried and which is highly reactive, freshly precipitated aluminum hydroxide containing some carbonate. Such aluminum hydroxide gel compounds are distinguished from the inert grade of aluminum hydroxide in which only aluminum and hydroxy and/or oxy entities are present by the fact that they are oxy-hydroxy bicarbonate-carbonate types of aluminum compounds. Each such compound is prepared by an alkaline precipitating reagent which contains either bicarbonate or carbonate as its anion. Each of the typical "reactive-grade aluminum hydroxide" compressed gels employed in the antacid suspensions either alone or in combination with other buffering entities, such as, for example, magnesium and/or calcium hydroxides, carbonates, silicates, and in some instances sodium and other compounds, are in reality mixed, complex, amorphous and highly hydrated systems of aluminum hydroxy carbonates and bicarbonates. The latter anionic moieties confer upon the gel the property of rapid reactivity with hydrochloric acid of gastric strength. Such compounds are distinguished from inert aluminum hydroxide by simple carbon dioxide evolution analysis. In accordance with the present invention such compounds will have at least 0.3 and preferably 0.5 mol of carbonate calculated as $CO_2$ for each mol of aluminum oxide. A preferred magnesium hydroxide gel is a 30 percent magnesium hydroxide paste obtained by controlled precipitation from pure aqueous solutions of magnesium sulfate and sodium hydroxide followed by filtration, washing and mixing the washed hydrogel. We may use other forms of $Mg(OH)_2$ as, for example, the lime (CaO) as dolomitic lime precipitate of $MgCl_2$.

The wet compressed gels of the aluminum hydroxide material which we use usually contain about ½ mol of $CO_2$ per mol of $Al_2O_3$, and the dried gels about 0.2 mol of $CO_2$ per mol of $Al_2O_3$. Our codried product has been found to contain about 5 to 50 percent by weight of the foodgrade di- or trihydroxy alcohol which is employed. The alcohol may be any water soluble foodgrade di- or trihydroxy alcohol. This includes 1:3 butylene glycol, 1,2 propylene glycol, polyethylene glycol, glycerin, etc. It does not include 1,3 propane diol which is not suitable for oral ingestion, and it does not include hexitols. The hexitols have been shown not to give the results which are attributed to our invention. When polyethylene glycol is used its molecular weight may be in the range of about 200 to 700. Although molecular weights of lower than 200 are possible they are not approved as foodgrade, and although molecular weights greater than 700 are usable their solubility in water is reduced making manipulation in the process difficult. Molecular weights of about 400 to 600 are preferred.

The invention will be further illustrated by a detailed description in connection with the following specific examples of the practice of it. In these examples and elsewhere herein the proportions are expressed as parts by weight unless specifically stated to the contrary.

The following examples illustrate the methods employed in the production of three basic types of resuspendable dried antacids, i.e., the system with the basic aluminum bicarbonate-carbonate system; combination with the basic magnesium basic carbonate; and $Al(OH)_3$ (basic aluminum bicarbonate-carbonate) - magnesium hydroxide systems.

$Al(OH)_3$ - Glycol Systems $Al(OH)_3$ gels referred to in the following examples 1–7 are in reality basic aluminum bicarbonate-carbonate systems.

EXAMPLE 1

F-1000 - 1:3 Butylene Glycol

Four parts Reheis F-1000 Compressed Gel U.S.P. (10% $Al_2O_3$), one part 1:3 Butylene Glycol, Food Grade, and three parts of deionized water were placed into suspension form and stirred rapidly at ambient temperatures for two hours. The suspension was then spray dried at 200 ml/min. employing an outlet temperature of 270° F.

A typical laboratory batch was prepared by placing 3,000g Reheis F-1000 Compressed Gel U.S.P. containing 10% $Al_2O_3$; 750g 1:3 Butylene Glycol, Food Grade; and 2,250g deionized water into a 10 liter battery jar (inside diameter 9¾"). The batch was put into suspension form with the aid of a Lightnin' overhead stirrer, employing a 4 inch, 6 blade turbine agitator, set at medium speed; a 1½ inch baffle is also used. Upon attainment of a homogeneous suspension (approximately 5 mins.), the agitator speed was set at high speed and the suspension stirred for 2 hours. The batch was then spray dried in a Bowen 3-foot, flat-bottom, laboratory spray dryer employing an outlet temperature of 270° F., and a feed rate of 200 ml/min. 370g of soft, finely divided, white powder were obtained. The dried gel analyzed as follows:

TABLE I

| Dried Gel | |
|---|---|
| $Al_2O_3$ | 44.3% |
| Acid Consuming Capacity | 268 cc N/10 HCl/g of powder |
| 1:3 Butylene Glycol | 22.9% |
| Apparent Density g/ml | 0.18 |

The antacid effectiveness was determined and appears in Table II. The method employed is a modification of the technique of Holbert, Noble and Grote, J. Amer. Pharm. Assoc., 37, 292, (1948) as described in U.S. Pat. No. 2,797,978.

TABLE II

| | In Vitro Measurement of Antacid Activity (1 gm. dose) | |
|---|---|---|
| | Prior Art | This Invention |
| Time (Min.) | F-1000 Dried Gel (Plant Batch) (pH) | F-1000 Resuspendable Dried Antacid (pH) |
| 0 | 1.7 | 2.0 |
| 0.4 | 1.7 | 2.7 |
| 0.9 | 1.7 | 3.5 |
| 1.4 | 1.7 | 3.8 |
| 1.8 | 1.8 | 3.9 |
| 10 | 1.9 | 3.9 |
| 20 | 1.9 | 4.0 |
| 30 | 2.0 | 4.0 |
| 40 | 2.1 | 4.0 |
| 50 | 2.1 | 4.0 |

An investigation into the resuspending characteristics of the aforementioned dried gel entailed reconstituting the dried gel at room temperature at a 4% $Al_2O_3$ concentration by suspending 148g of the dried gel with 1,452g deionized water in an 8" diameter battery jar with the aid of an Eppenbach homo-mixer Laboratory Model 1-L (turbine diameter = 1.719"), at 2,500 rpm for 30 min. A 90 ml aliquot was then taken, placed into a 3½" × 2½" × 1" oblong bottle resulting in a 2⅜" fill, and observed.

A plant produced Reheis F-1000 Dried Gel was similarly treated; comparative data is listed in Table III.

As a further means of demonstrating the resuspending attributes of the captioned antacid, a 4% $Al_2O_3$ suspension was achieved by placing 3.7g. of our antacid powder and 36.3g deionized water into a 4" × 1" glass vial resulting in a 3¼" fill, and then simply hand shaking the capped vial 10 times. Here again, Reheis F-1000 Dried Gel was similarly treated and the comparative data is listed in Table III.

TABLE III

| Reconstituted Dried Gels | | |
|---|---|---|
| Dried Gel | Method of Stirring | Observations |
| F-1000-1:3 Butylene Glycol | 30 minutes stirring cycle using an Eppenbach Homo-Mixer at 2,500 rpm | 15 min. observations: no separation; gel-like feel 24 hr. observation: ⅛" separation; no caking; gel-like |
| | Hand shaken (10 shakes) | 15 min. observation: no separation; smooth feel 24 hr. observation ⅝" separation; no caking; gel-like |
| Reheis F-1000 | 30 minutes stirring cycle using an Eppenbach Homo-Mixer at 2,500 rpm | 15 min. observation: ¼" cake 24 hr. observation; ½" cake; ¾ separation |
| | Hand shaken (10 shakes) | 15 min. observation: ½" cake; slightly gritty feel 24 hr. observation ⅝" cake |

EXAMPLE 2

F-1000 - Propylene Glycol

The concentrations and procedures (both manufacturing and testing) employed in Example 1 were duplicated with the exception that Propylene Glycol U.S.P. Grade was used in lieu of 1:3 Butylene Glycol.

Approximately ¾ lb. of soft, finely divided, white powder was obtained, with the following assay.

TABLE IV

| | |
|---|---|
| $Al_2O_3$ | 41.8% |
| Acid Consuming Capacity | 255 cc N/10 HCl/g of powder |

TABLE IV-continued

| | |
|---|---|
| Propylene Glycol | 25.8% |
| Apparent Density g/l. | 0.20 |

The superior antacid effectiveness of the resuspended gel was determined as in the case of Example 1.

Upon reconstitution, this dried gel exhibited the following properties listed in Table V.

TABLE V

| Dried Gel | Method of Stirring | Observations |
|---|---|---|
| F-1000-Propylene Glycol | 30 minutes stirring cycle using an Eppenbach Homo-Mixer at 2,500 rpm | 15 min. observation: no separation; gel-like feel. 24 hr. observation: ⅛" separation; no caking; gel-like |
| | Hand Shaken (10 shakes) | 15 min. observation: no separation; smooth feel 24 hr. observation: ½" separation; no caking; gel-like |
| Reheis F-1000 | Reported in Table III | |

EXAMPLE 3

F-500 - Propylene Glycol

The procedure of Example 1 was duplicated except that Reheis F-500 Compressed Gel U.S.P. was used in lieu of F-1000 Gel, and Propylene Glycol U.S.P. was used in lieu of 1:3 Butylene Glycol.

An approximate ¾ lb. yield of a soft, finely divided, white powder was obtained, with the following assay.

TABLE VI

| | |
|---|---|
| $Al_2O_3$ | 43.5% |
| Acid Consuming Capacity | 245 cc N/10 HCl/g of powder |
| Propylene Glycol | 26.0% |
| Apparent Density | 0.3 gram/cc |
| Reaction Velocity (Reheis) | 10 secs. |

The antacid effectiveness was determined and found to be superior to the prior art dried gel.

The rehydrating attributes of this material are described in Table VII.

TABLE VII

| Dried Gel | Method of Stirring | Observations |
|---|---|---|
| F-500-Propylene Glycol | 30 minutes stirring cycle using an Eppenbach Homo-Mixer at 2,500 rpm | 15 min. observation: no separation; gel-like feel 24 hr. observation; ¼" separation; no caking; gel-like |
| | Hand shaken (10 shakes) | 15 min. observation: no separation; smooth feel 24 hr. observation: ⅞" separation; no caking; gel-like |
| Reheis F-500 | 30 minutes stirring cycle using an Eppenbach Homo-Mixer at 2,500 rpm | 15 min. observation: 1½" separation; smooth feel 24 hr. observation: 1½" separation; no caking; smooth feel |
| | Hand shaken (10 shakes) | 15 min. observation: 2" separation; ⅛" cake; smooth feel 24 hr. observation: 2¼" separation; ⅛" cake; smooth feel |

EXAMPLE 4

F-2000 - Propylene Glycol

The procedure of Example 3 was duplicated except that 2.67 parts Reheis F-2000 Gel U.S.P. (13.0% $Al_2O_3$), 1 part Propylene Glycol and 4.34 parts of deionized water were used in lieu of 4 parts F-500 Gel, 1 part propylene glycol and 3 parts deionized water. A laboratory preparation of this Example employed the following reagents:

2,000 g Reheis F-2000 Gel U.S.P. (13.0% $Al_2O_3$)
750 g Propylene Glycol U.S.P.
3,250 g deionized water An approximate yield of ¾ lb. of a soft, finely divided, white powder was obtained, with the following assay.

TABLE VIII

| | |
|---|---|
| $Al_2O_3$ | 47.9% |
| Acid Consuming Capacity | 266 cc N/10 HCl/g of powder |
| Propylene Glycol | 21.5% |

Upon reconstitution, this dried gel exhibited the following properties listed in Table IX.

TABLE IX

| Dried Gel | Method of Stirring | Observations |
|---|---|---|
| F-2000-Propylene Glycol | 30 minutes stirring cycle using an Eppenbach Homo-Mixer at 2,500 rpm | 15 min. observation: no separation; gel-like feel 24 hr. observation: 1/8" separation; no caking; gel-like |
| | Hand shaken (10 shakes) | 15 min. observation: no separation; smooth feel 24 hr. observation: 3/4" separation; no caking; gel-like |
| Reheis F-2000 | 30 minutes stirring cycle using an Eppenbach Homo-Mixer at 2,500 rpm | 15 min. observation: 1/8" cake; slightly gritty feel 24 hr. observation: 5/16" cake |
| | Hand shaken (10 shakes) | 15 min. observation: 1/4" cake; slightly gritty feel 24 hr. observation: 1/4" separation; 9/16" cake |

EXAMPLE 5

F-500 - Propylene Glycol

The procedure of Example 3 was duplicated except that the ratio of gel to propylene glycol was 1:1, water excluded, and stirring time increased to 20 hours.

A typical laboratory preparation of this Example employed the following reagents:

3,000 g Reheis F-500 Gel U.S.P.
3,000 g Propylene Glycol U.S.P.

An approximate yield of ¾ lb. of a soft, finely divided, white powder was obtained, with the following assay.

TABLE X

| | |
|---|---|
| $Al_2O_3$ | 37.9% |
| Acid Consuming Capacity | 230 cc N/10 HCl/g of powder |
| Propylene Glycol | 29.2% |
| Apparent Density | 0.32 g/cc |
| Reaction Velocity (Reheis) | 16 secs. |

The rehydrating attributes of this material are described in Table XI.

TABLE XI

| Dried Gel | Method of Stirring | Observations |
|---|---|---|
| F-500-Propylene Glycol | 30 minutes stirring cycle using an Eppenbach Homo-Mixer at 2,500 rpm | 15 min. observation: no separation; gel-like feel<br>24 hr. observation: ⅛" separation; no caking; gel-like |
| | Hand shaken (10 shakes) | 15 min. observation: no separation; smooth feel<br>24 hr. observation: ¼" separation; no caking; gel-like |
| Reheis F-500 | Reported in Table VII | |

EXAMPLE 6

F-X - Propylene Glycol

The procedure of Example 2 was duplicated except that Reheis F-X Gel was used in lieu of F-1000 Gel, incorporating the following concentrations: 8.75 parts F-X Gel, 1 part propylene glycol, and 4.06 parts deionized water. Reheis F-X Gel designates the specific type of gel obtained by essentially reversing the order of addition used in the preparation of F-1000 Gel. Specifically, the production of F-1000 Gel requires the addition of $AlCl_3$ to soda ash (acid to base), while F-X Gel requires the reverse addition, that is, soda ash to $AlCl_3$ (base to acid). A typical laboratory preparation of this Example employed the following reagents:

2,800 g Reheis F-X Gel (4.2% $Al_2O_3$)

320 g Propylene Glycol U.S.P.

1,300 g deionized water

An approximate yield of ½ lb. of a soft, finely divided, white powder was obtained, with the following assay.

TABLE XII

| | |
|---|---|
| $Al_2O_3$ | 43.3% |
| Acid Consuming Capacity | 266 cc N/10 HCl/g of powder |
| Propylene Glycol | 29.2% |

The rehydrating attributes of this material are described in Table XIII.

TABLE XIII

| Dried Gel | Method of Stirring | Observations |
|---|---|---|
| F-X-Propylene Glycol | 30 minutes stirring cycle using an Eppenbach Homo-Mixer at 2,500 rpm | 15 min. observation: 1-1/8" separation; no caking; smooth feel<br>24 hr. observation: 1-5/16" separation; no caking; smooth feel |
| | Hand shaken (10 shakes) | 15 min. observation: 1-5/16" separation; no caking; smooth feel<br>24 hr. observation: 2-1/2" separation; no caking; smooth feel |
| Reheis F-X | 30 minutes stirring cycle using an Eppenbach Homo-Mixer at 2,500 rpm | 15 min. observation: 2" separation; 1/8 cake; gritty<br>24 hr. observation: 2" separation; 1/8" cake; gritty; no gel-like attributes |
| | Hand shaken (10 shakes | 15 min. observation: 3" separation; trace cake; gritty feel<br>24 hr. observation: 3" separation; 1/16" cake; gritty feel; no gel-like attributes |

EXAMPLE 7

F-1000 - 1:3 Butylene Glycol

The procedure of Example 1 was duplicated except for the use of 20 parts of F-1000 Gel, 1 part 1:3 Butylene Glycol and 3 parts deionized water. A laboratory preparation of this Example, therefore, employed the following reagents:

3,000 g Reheis F-1000 Gel U.S.P. (10.17% $Al_2O_3$)

150 g. 1:3 Butylene Glycol 2,850 g. deionized water

An approximate yield of ¾ lb. of a soft, finely divided, white powder was obtained, with the following assay:

TABLE XIV

| | |
|---|---|
| $Al_2O_3$ | 47.3% |
| Acid Consuming Capacity | 271 cc N/10 HCl/g of powder |
| 1:3 Butylene Glycol | 18.2% |
| Apparent Density | 0.24 g/cc |

The rehydrating attributes of this material are described in Table XV.

TABLE XV

| Dried Gel | Method of Stirring | Observations |
|---|---|---|
| F-1000-1:3 Butylene Glycol | 30 minutes stirring cycle using an Eppenbach Homo-Mixer at 2,500 rpm | 15 min. observation: 1/16" separation; no caking; smooth feel<br>24 hr. observation: 3/8" separation; no caking; smooth feel |
| | Hand shaken (10 shakes) | 15 min. observation: 3/4" separation; no caking; smooth feel<br>24 hr. observation: 1.1/2" separation; no caking; smooth feel |
| Reheis F-1000 | Reported in Table III | |

**F-MA 11 - Glycol Systems

** F-MA 11 is a combined gel of aluminum basic bicarbonate-carbonate and magnesium basic carbonate (U.S. Pat. No. 2,797,978). Varying quantities of magnesium basic carbonate may be added to or precipitated in the presence of the aluminum basic carbonates-bicarbonates as outlined in this patent.

EXAMPLE 8

The procedure employed in Example 1 was followed in which sufficient 1:3 Butylene Glycol was admixed with Reheis F-MA 11 Gel and deionized water to yield a suspension containing 3.3% $Al_2O_3$ and weight ratios of:

Ratios of $Al_2O_3$, MgO and 1,3 butylene glycol were 1.0/0.19/1.32.

A typical laboratory preparation of this Example employed the following reagents:

3,000 g Reheis F-MA 11 Gel (6.7% $Al_2O_3$ and 1.3% MgO)

264.8 g 1.3 Butylene Glycol Food Grade 2,735.2 g. deionized water

An approximate yield of ¾ lb. of a soft, finely divided, white powder was obtained with the following assay:

TABLE XVI

| | |
|---|---|
| $Al_2O_3$ | 32.5% |
| MgO | 7.1% |
| Acid Consuming Capacity | 254 cc N/10 HCl/g of powder |
| 1:3 Butylene Glycol | 20.3 % |
| Apparent Density g/ml | 0.35 |

The rehydrating attributes of this material are described in Table XVII.

TABLE XVII

| Dried Gel | Method of Stirring | Observations |
|---|---|---|
| F-MA 11-1:3 Butylene Glycol | 30 minutes stirring cycle using an Eppenbach Homo-Mixer at 2,500 rpm | 15 min. observation: 1/16" separation; no caking; smooth feel 24 hr. observation: 1/4" separation; no caking; smooth feel |
| | Hand shaken (10 shakes) | 15 min. observation: 5/8" separation; no caking; smooth feel 24 hr. observation: 1" separation; no caking; smooth feel |
| Reheis F-MA 11 | 30 minutes stirring cycle using an Eppenbach Homo-Mixer at 2,500 rpm | 15 min. observation: 1/4" separation; no caking; slightly gritty 24 hr. observation: 1-1/2" separation; no caking; slightly gritty feel |
| | Hand shaken (10 shakes) | 15 min. observation: 1-1/2" separation; no caking; slightly gritty 24 hr. observation: 2" separation; 1/8" cake; slightly gritty feel |

EXAMPLE 9

F-MA 11 - Propylene Glycol

The procedure of Example 8 was followed except that Propylene Glycol was used in lieu of 1:3 Butylene Glycol.

An approximate yield of ¾ lb. of a soft, finely divided, white powder was obtained with the following assay:

TABLE XVIII

| | |
|---|---|
| $Al_2O_3$ | 35.5% |
| MgO | 7.1% |
| Acid Consuming Capacity | 261 cc N/10 HCl/g of powder |
| Propylene Glycol | 18.1% |

The rehydrating attributes of this material are described in Table XIX.

TABLE XIX

| Dried Gel | Method of Stirring | Observations |
|---|---|---|
| F-MA 11-Propylene Glycol | 30 minutes stirring cycle using an Eppenbach Homo-Mixer at 2,500 rpm | 15 min. observation: 1/16" separation; no caking; gel-like feel 24 hr. observation: 3/8" separation; no caking; gel-like feel |
| | Hand shaken (10 shakes) | 15 min. observation: 1/8" separation; no caking; smooth feel 24 hr. observation: 1/2" separation; no caking; smooth feel |
| Reheis F-MA 11 | Reported in Table XVII | |

$Al(OH)_3$ - $Mg(OH)_2$ - Glycol Systems

EXAMPLE 10

F-1000 - $Mg(OH)_2$ - 1:3 Butylene Glycol

The procedure employed in Example 1 was followed in which sufficient 1:3 Butylene Glycol, deionized water, F-1000 Gel, and Reheis $Mg(OH)_2$ paste (gel) form were admixed to yield a suspension containing 2.5% $Al_2O_3$ and weight ratios of: Ratios of $Al_2O_3$, MgO and 1,3 butylene glycol were 1.0/1.0/3.1.

A typical laboratory preparation of this Example employed the following reagents:

1,485 g Reheis F-1000 Gel (10.1% $Al_2O_3$)
622 g Reheis $Mg(OH)_2$ paste (24.1% MgO)
467.5 g 1:3 Butylene Glycol, Food Grade
3,425.5 g deionized water An approximate yield of ¾ lb. of a soft, finely divided, white powder was obtained with the following assay:

| | |
|---|---|
| $Al_2O_3$ | 28.1% |
| MgO | 28.6% |
| Acid Consuming Capacity | 280 cc N/10 HCl/g of powder |
| Apparent Density | 0.18 g/cc |
| 1:3 Butylene Glycol | 13.0% |

The rehydrating attributes of this material at a 2.5% $Al_2O_3$ concentration are described in Table XXI.

TABLE XXI

| Dried Gel | Method of Stirring | Observations |
|---|---|---|
| F-1000-$Mg(OH)_2$-1:3 Butylene Glycol | 30 minutes stirring cycle using an Eppenbach Homo-Mixer at 2,500 rpm | 15 min. observation: no separation; gel-like feel 24 hr. observation: 1/8" separation; no caking; gel-like feel |
| | Hand shaken (10 shakes) | 15 min. observation: no separation; no caking; smooth feel 24 hr. observation: 7/16" separation; no caking; smooth feel |
| F-1000-$Mg(OH)_2$ | 30 minutes stirring cycle using an Eppenbach Homo-Mixer at 2,500 rpm | 15 min. observation: 3/16" separation; no caking; smooth feel 24 hr. observation: 5/8" separation; no caking; smooth feel |
| | Hand shaken (10 shakes) | 15 min. observation: 1" separation; 1/8" cake; smooth feel 24 hr. observation: 2" separation; 1/8" cake; smooth feel |

EXAMPLE 11

F-1000 - $Mg(OH)_2$ - Propylene Glycol

The procedure of Example 10 was followed except that Propylene Glycol U.S.P. was used in lieu of 1:3 Butylene Glycol.

1,485 g Reheis F-1000 Gel (10.1% $Al_2O_3$)
622 g Reheis $Mg(OH)_2$ paste (24.1% MgO)
467.5 g Propylene Glycol U.S.P.
3,425.5 g deionized water An approximate yield of ¾ lb. of a soft, finely divided, white powder was obtained with the following assay:

TABLE XXII

| | |
|---|---|
| $Al_2O_3$ | 28.3% |
| MgO | 28.8% |
| Acid Consuming Capacity | 283.5 cc N/10 HCl/g of powder |
| Apparent Density | 0.19 g/cc |
| Propylene Glycol | 13.7% |

The rehydrating attributes of this material are described in Table XXIII.

TABLE XXII

| | |
|---|---|
| $Al_2O_3$ | 28.3% |
| MgO | 28.8% |
| Acid Consuming Capacity | 283.5 cc N/10 HCl/g of powder |
| Apparent Density | 0.19 g/cc |
| Propylene Glycol | 13.7% |

TABLE XXIII

| Dried Gel | Method of Stirring | Observations |
|---|---|---|
| F-1000 $Mg(OH)_2$ | 30 minutes stirring cycle using an Eppenbach Homo- | 15 min. observation: no separation; gel- |

TABLE XXIII-continued

| Dried Gel | Method of Stirring | Observations |
|---|---|---|
| Propylene Glycol | Mixer at 2,500 rpm | like feel 24 hr. observation: 1/8" separation; no caking; gel-like feel |
| | Hand shaken (10 shakes) | 15 min. observation: no separation; no caking; smooth feel 24 hr. observation: 1/2" separation; no caking; smooth feel |
| F-1000-$Mg(OH)_2$ | Recorded in Table XXI | |

EXAMPLE 12

F-1000 - $Mg(OH)_2$ - Propylene Glycol

The procedure of Example 10 was followed except that sufficient quantities of F-1000 Gel, $Mg(OH)_2$ paste, propylene glycol, and deionized water were admixed to yield a suspension containing 2.4% $Al_2O_3$, 2.7% MgO and weight ratios of $Al_2O_3$, MgO and propylene glycol of 1.0/1.12/2.86.

A typical laboratory preparation of this Example employed the following reagents:

1,372 g Reheis F-1000 Gel (10.5% $Al_2O_3$)
670 g Reheis $Mg(OH)_2$ paste (24.2% MgO)
413 g Propylene Glycol U.S.P.
3,545 g deionized water An approximate yield of 3/4 lb. of a soft, finely divided, white powder was obtained with the following assay:

TABLE XXIV

| | |
|---|---|
| $Al_2O_3$ | 24.9% |
| MgO | 28.7% |
| Acid Consuming Capacity | 292 cc N/10 HCl/g of powder |
| Propylene Glycol | 14.5% |

The rehydrating attributes of this material are described in Table XXV.

TABLE XXV

| Dried Gel | Method of Stirring | Observations |
|---|---|---|
| F-1000-$Mg(OH)_2$-Propylene Glycol | 30 minutes stirring cycle using an Eppenbach Homo-Mixer at 2,500 rpm | 15 min. observation: no separation; gel-like feel 24 hr. observation: 1/8" separation; no caking; gel-like feel |
| | Hand shaken (10 shakes) | 15 min. observation: no separation; smooth feel 24 hr. observation: 7/16" separation; smooth feel; no caking |
| F-1000-$Mg(OH)_2$ | Recorded in Table XXI | |

EXAMPLE 13

F-500 - Propylene Glycol Resuspendable Dried Antacid (Example 3) + $Mg(OH)_2$ Paste (Gel) Form Sufficient quantities of F-500 - Propylene Glycol Resuspendable Dried Antacid (Example 3), $Mg(OH)_2$ paste (Gel) Form, and deionized water necessary to effect a 2.4% $Al_2O_3$
and 2.7% MgO suspension were formulated by admixing 64 g of Example 3 with 850 ml deionized water, with the aid of an Eppenbach Homo-Mixer Laboratory Model 1-L at 2,000 rpm for approximately 5 minutes; 86 g Reheis $Mg(OH)_2$ paste (31.6% MgO) is then added and the suspension stirred at 2,000 rpm for 15 minutes.

A stable, gel-like suspension was obtained which exhibited similar suspension and gel characteristics to that of a control suspension prepared with F-500 Gel and $Mg(OH)_2$ Paste.

$Al(OH)_3$ - Glycerin Systems

EXAMPLE 14

F-100 - Glycerin -Resuspendable Dried Antacid

The procedure of Example 1 was duplicated except that one part Reheis F-1000 Compressed Gel U.S.P. and one part Glycerin U.S.P. were the only reagents used. The feed rate during spray drying was also reduced to 100 ml./min..

Preparation of this Example employed the following reagents:

3,000 g Reheis F-1000 Gel (10.1% $Al_2O_3$)
3,000 g Glycerin U.S.P.

An approximate yield of 1 lb. of a soft, finely divided, white powder was obtained with the following assay:

TABLE XXVI

| | |
|---|---|
| $Al_2O_3$ | 25.7% |
| Acid Consuming Capacity | 145 mls of N/10 HCl/per gram |
| Apparent Density | 0.36 |
| Glycerin | 59.3% |

The rehydrating attributes of this material at 10% solids concentration are described in Table XXVII.

TABLE XXVII

| Dried Gel | Method of Stirring | Observations |
|---|---|---|
| F-1000-Glycerin | Hand shaken (10 shakes) | 15 min. observation: 5/8" separation; no caking; smooth feel 24 hr. observation: 2-1/4" separation; no caking; smooth feel |

In all of the above examples, the antacid effectiveness was found to be superior for the reconstituted gel when compared to the same weight does of the prior art dried gel.

EXAMPLE 15

F-1000 - Glycerin, Tray Dried

The procedure of Example 1 was followed except that forty parts Reheis F-1000 Compressed Gel U.S.P., one part Glycerin U.S.P., and thirty-nine parts deionized water were used and the resultant suspension tray dried by placing 1 kilogram of slurry into a 6" × 10" × 2" pyrex dish and placing said dish into an air circulating oven set at 105° F. for 48 hours. The dried cake was then ground to 40 mesh.

A soft, white powder was obtained, with the following assay:

TABLE XXVIII

| | |
|---|---|
| $Al_2O_3$ | 44.4% |
| Glycerin | 9.6% |
| Acid Consuming Capacity | 250 cc N/10 HCl/g of powder |
| Apparent Density g/m. | 0.32 |

The antacid effectiveness of the resuspended gel was determined and appears in Table XXIX.

TABLE XXIX

| Time (min.) | Prior Art F-1000 Dried Gel (Plant Batch) (pH) | This Invention F-1000-Glycerin Dried Antacid (pH) |
|---|---|---|
| 0 | 1.7 | 1.6 |
| 0.5 | 1.7 | 3.1 |
| 1.0 | 1.7 | 3.5 |
| 1.5 | 1.7 | 3.65 |

TABLE XXIX-continued

| Time (min.) | Prior Art F-1000 Dried Gel (Plant Batch) (pH) | This Invention F-1000-Glycerin Dried Antacid (pH) |
|---|---|---|
| 1.8 | 1.8 | 3.75 |
| 10.0 | 1.9 | 3.90 |
| 20.0 | 1.9 | 3.9 |
| 30.0 | 2.0 | 3.0 |
| 40.0 | 2.1 | 3.85 |
| 50.0 | 2.1 | 3.80 |

The rehydrating attributes of this material are described in Table XXX.

TABLE XXX

| Dried Gel | Method of Stirring | Observations |
|---|---|---|
| F-1000-Glycerin (tray dried) | 30 minutes stirring cycle using an Eppenbach Homo-Mixer at 2,500 rpm | 24 hr. observation: 1/16: separation; no caking; gel-like |
| Reheis F-1000 | Reported in Table III | |

EXAMPLE 16

F-1000 - $Mg(OH)_2$ - Glycerin, Tray Dried

The procedure of Example 15 was followed except that twenty-five and two-tenths parts Reheis F-1000 Compressed Gel, fourteen and eight-tenths parts Reheis $Mg(OH)_2$ paste, one part Glycerin U.S.P., and thirty-nine parts deionized water were used.

A soft, white powder was obtained with the following assay:

TABLE XXXI

| | |
|---|---|
| $Al_2O_3$ | 21.9% |
| MgO | 34.9% |
| Glycerin | 7.8% |
| Acid Consuming Capacity | 292 cc N/10 HCl/g of powder |
| Apparent Density g/ml | 0.35 |

The antacid effectiveness was determined and appears in Table XXXII.

TABLE XXXII

| Time (min.) | Prior Art F-1000 Dried Gel (Plant Batch) (pH) | This Invention F-1000-Glycerin Dried Antacid (pH) |
|---|---|---|
| 0 | 1.7 | 1.6 |
| 0.5 | 1.7 | 3.85 |
| 1.0 | 1.7 | 4.25 |
| 1.5 | 1.7 | 4.65 |
| 1.8 | 1.8 | 5.2 |
| 10.0 | 1.9 | 6.3 |
| 20.0 | 1.9 | 5.0 |
| 30.0 | 2.0 | 5.1 |
| 40.0 | 2.1 | 5.0 |
| 50.0 | 2.1 | 4.9 |

The rehydrating attributes of this material are described in Table XXXIII.

TABLE XXXIII

| Dried Gel | Method of Stirring | Observations |
|---|---|---|
| F-1000-$Mg(OH)_2$-Glycerin | 30 minutes stirring cycle using an Eppenbach Homo-Mixer at 2,500 rpm | 24 hr. observation: 1/16" separation; no caking; gel-like |
| F-1000-$Mg(OH)_2$ | Recorded in Table XXI. | |

EXAMPLE 17

F-1000 - Glycerin, Rotary Drum Dried

The procedure of Example 1 was followed except that eight parts Reheis F-1000 Compressed Gel U.S.P., one part Glycerin U.S.P. and three parts deionized water were used.

The resultant suspension was dried in a laboratory model Double Drum Dryer at a drum speed of 3 rpm and drum surface temperature of 300° F.

A soft, white, moderately fine granular material was obtained with the following assay:

TABLE XXXIV

| | |
|---|---|
| $Al_2O_3$ | 35.5% |
| Glycerin | 38.0% |
| Acid Consuming Capacity | 208 cc N/10 HCl/g of material |
| Apparent Density g/ml | 0.31 |

The antacid effectiveness of the resuspended gel was determined and appears in Table XXXV.

TABLE XXXV

| Time (min.) | Prior Art F-1000 Dried Gel (Plant Batch) (pH) | This Invention F-1000-glycerin Dried Antacid (pH) |
|---|---|---|
| 0 | 1.7 | 1.6 |
| 0.5 | 1.7 | 4.15 |
| 1.0 | 1.7 | 4.20 |
| 1.5 | 1.7 | 4.20 |
| 1.8 | 1.8 | 4.20 |
| 10.0 | 1.9 | 4.25 |
| 20.0 | 1.9 | 4.25 |
| 30.0 | 2.0 | 4.25 |
| 40.0 | 2.1 | 4.20 |
| 50.0 | 2.1 | 4.20 |

The rehydrating attributes of this material are described in Table XXXVI.

TABLE XXXVI

| Dried Gel | Method of Stirring | Observations |
|---|---|---|
| F-1000-Glycerin (Rotary Drum Dried) | 30 minutes stirring cycle using an Eppenbach Homo-Mixer at 2,500 rpm | 24 hr. observation: 1/16" separation; no caking; gel-like |
| Reheis F-1000 | Reported in Table III | |

EXAMPLE 18

F-1000 - Glycerin - Resuspendable Dried Antacid

The procedure of Example 1 was duplicated except that eight parts Reheis F-1000 Compressed Gel U.S.P., one part Glycerin U.S.P. and three parts well water were used. The batch was put into suspension form with the aid of a Hobart Model N-50 stirrer set at low speed initially until a homogeneous suspension was attained (approximately 5 mins.), and then stirred at medium speed for 0.5 hour. The batch was then spray dried as in Example 1.

A soft, white powder was obtained with the following assay:

TABLE XXXVII

| | |
|---|---|
| $Al_2O_3$ | 33.9% |
| Glycerin | 36.0% |
| Acid Consuming Capacity | 186 cc N/10 HCl/g of powder |
| Apparent Density g/ml | 0.35 |

The antacid effectiveness was determined and appears in Table XXXVIII.

TABLE XXXVIII

| Time (min.) | Prior Art F-1000 Dried Gel (Plant Batch) (pH) | This Invention F-1000 - Glycerin Dried Antacid (pH) |
|---|---|---|
| 0 | 1.7 | 1.6 |
| 0.5 | 1.7 | 3.7 |
| 1.0 | 1.7 | 3.9 |
| 1.5 | 1.7 | 3.9 |
| 1.8 | 1.8 | 3.95 |
| 10.0 | 1.9 | 4.0 |
| 20.0 | 1.9 | 4.0 |

TABLE XXXVIII-continued

| Time (min.) | Prior Art F-1000 Dried Gel (Plant Batch) (pH) | This Invention F-1000 - Glycerin Dried Antacid (pH) |
|---|---|---|
| 30.0 | 2.0 | 4.0 |
| 40.0 | 2.1 | 4.0 |
| 50.0 | 2.1 | 3.95 |

The rehydrating attributes of this material are described in Table XXXIX.

TABLE XXXIX

| Dried Gel | Method of Stirring | Observations |
|---|---|---|
| F-1000 Glycerin | 30 minutes stirring cycle using an Eppenbach Homo-Mixer at 2,500 rpm | 24 hr. observation: 1/16" separation; no caking; gel-like |
| Reheis F-1000 | Reported in Table III | |

EXAMPLE 19

The rehydrating attributes of the titled antacids can also be demonstrated by the following gelation test:

Antacid powder is slowly added in 0.5 gram increments to a tared 150 ml beaker ID=2.0 inches containing 50.0 grams deionized water and a 1½ inch magnetic bar which is mounted upon a magnetic stirrer set at medium speed. The end point is attained upon complete gelation of the resultant suspension within one to two hours. The gel so obtained is virtually identical to the precursor gel from which the dried resuspendable powder was prepared. In applying the above test, the product from Example 2 reverted to a comparable Reheis F-1000 Gel at an $Al_2O_3$ concentration of 10.4%.

EXAMPLE 20

The following reagents were employed:

2,000 grams Reheis F-1000 Gel (10.5% $Al_2O_3$)
292 grams $MgCO_3$ paste (10.8% MgO)
28 grams Glycerin U.S.P.
1,500 grams well water The basic $MgCO_3$ paste was prepared by adding $CO_2$ gas to Reheis $Mg(OH)_2$ slurry to form $Mg(HCO_3)_2$ solution. The bicarbonate solution was filtered to remove impurities and then heated to precipitate basic $MgCO_3$.

The same procedure was employed as in Example 1. The glycerine, well water, F-1000 Gel, and basic $MgCO_3$ paste were mixed to yield a suspension containing 5.5% $Al_2O_3$. Ratios of $Al_2O_3$, MgO and glycerine were 1.0/0.15/0.13.

The procedure yielded approximately ¾ pound of a soft, finely divided, white powder with the following assay:

| | |
|---|---|
| $Al_2O_3$ | 41.5% |
| MgO | 6.5% |
| Glycerin | 6.9% |
| Acid Consuming Capacity | 274 cc N/10 HCl/gram of powder |
| Apparent Density | 0.33 g/cc |

The antacid effectiveness and rehydrating attribute of the reconstituted gel was found superior when compared with reconstituted gel of the type previously known to the art.

EXAMPLE 21

The following reagents were employed:

1,190 grams Reheis F-1000 Gel (10.5% $Al_2O_3$)
927 grams $MgCO_3$ paste (10.8% MgO)
28 grams Glycerin U.S.P.
1,500 grams well water The procedure of Example 20 was employed to obtain a yield of approximately ¾ pound of a soft, finely divided, white powder with the following assay:

| | |
|---|---|
| $Al_2O_3$ | 21.4% |
| MgO | 19.3% |
| Glycerin | 5.9% |
| Acid Consuming Capacity | 209 cc N/10 HCl/gram of powder |
| Apparent Density | 0.33 g/cc |

The antacid effectiveness and rehydrating attribute of the reconstituted gel was found superior when compared with with a reconstituted gel of the type previously known to the art.

EXAMPLE 22

Tests on Various Resuspendable Dried Gel Formulations

Tests were performed on samples of resuspendable dried gel preparations prepared in accordance with Examples contained herein. Samples were prepared in accordance with the following procedure based upon the formulations given in Table XXXX.

Procedure

A sufficient quantity of the dried antacid powders necessary to obtain the desired $Al_2O_3$ and magnesium oxide contents (where indicated) was added to deionized water containing the given amounts of dissolved parasepts and other additives.

The suspensions were then stirred for 30 minutes at a speed of 2,500 rpm using an Eppenbach "Homo-Mixer" Laboratory Model 1-L, turbine diameter = 1.719.

In all cases, 340 mls of suspension was placed into a 12 oz., clear Blake bottle and capped. The solid-resuspension properties were observed over a period of several months at ambient temperatures; and in all cases, highly gelatinous, highly suspended liquids resulted which had the appearance and mouth-feel of undried wet-gel suspensions.

TABLE XXXX

| Entity | Ex. 18 F-1000-Glycerin | Ex. 10 MgOl/$Al_2O_3$ 1:1 w/w; Butylene Glycol | Ex. 16 1.58/1,0 w/w $MgO/Al_2O_3$; Glycerin | Ex. 18 F-1000-Glycerin | Ex. 8 F-MA 11 Butylene Glycol |
|---|---|---|---|---|---|
| Resuspendable Dried Antacid (Weight) | 7.5 | 9.0 | 10.0 | 12.0 | 12.5 |
| $H_2O$ | 73.0 | 88.8 | 86.8 | 85.8 | 85.3 |
| Sorbitol 70% Solution | 5.0 | 2.0 | 3.0 | 2.0 | 2.0 |
| Glycine, N.F. | 2.0 | — | — | — | — |
| Magnesium Hydroxide Paste (21% MgO) | 12.3 | — | — | — | — |
| Parasepts* | 0.2 | 0.2 | 0.2 | 0.2 | 0.2 |
| Flavors | q.s | q.s | q.s | q.s | q.s |

*Composed of: 6.6 parts methyl parasept, 1 part propyl parasept

EXAMPLE 23

To demonstrate the effect on resuspendability of utilizing a predried gel in comparison with a fresh wet gel as used in the present invention, the following test was carried out:

A wet aluminum hydroxide gel which is aluminum hydroxide at 10% $Al_2O_3$, was reslurried employing propylene glycol and deionized water to a 5% $Al_2O_3$ and spray dried. A sample of the product was designated by the code R-089-13.

The same wet gel as used in preparing sample R-089-13 was reslurried to a 5% $Al_2O_3$ employing deionized water and spray dried. 100 grams of the dried powder, 20 grams of glycerin and 100 grams of deionized water were kneaded and tray dried with hot air at 50° C. and pulverized. A sample of the product was designated by the code R-087-96.

10% suspensions were prepared by putting 4 grams each of samples R-089-13 and R-087-96 and 36 ml deionized water into two separate 4" × 1" glass vials and hand shaking the capped vials 20 times to effect the suspension. Stability of the suspensions is tabulated as follows:

| SAMPLE R-089-13 | Age of Suspension (Time in Minutes) | | | | | |
|---|---|---|---|---|---|---|
| | 5 min. | 10 min. | 15 min. | 30 min. | 45 min. | 60 min. |
| Suspension | 100% | 100% | 100% | 97.7% | 96.5% | 96.5% |
| Supernatant | 0% | 0% | 0% | 2.3% | 3.5% | 3.5% |
| Cake | 0.0% | 0.0% | 0.0% | 0.0% | 0.0% | 0.0% |

| SAMPLE R-087-96 | Age of Suspension (Time in Minutes) | | | | | |
|---|---|---|---|---|---|---|
| | 5 min. | 10 min. | 15 min. | 30 min. | 45 min. | 60 min. |
| Suspension | 18.4% | 0.0% | 0.0% | 0.0% | 0.0% | 0.0% |
| Supernatant | 79.8% | 77.7% | 73.9% | 72.1% | 70.0% | 70.0% |
| Cake | 1.8% | 22.3% | 26.1% | 27.9% | 30.0% | 30.0% |

After 1 hour the suspension prepared from sample R-089-13 showed only 3.5% by volume of separation from the resuspended fraction into the supernatant fraction, while the suspension prepared from sample R-087-96 showed a 70% separation.

EXAMPLE 24

Although the use of propylene glycol is preferred as the alcohol and spray drying is preferred in the codrying step, the experiment of Example 23 was repeated using glycerin as the alcohol and tray drying in the codrying step as follows:

The same wet gel as used for starting material in Example 23 at 10% $Al_2O_3$, was needed with U.S.P. glycerin in a ratio of 50 parts of gel to 2 parts of glycerin (to obtain a glycerin concentration of 100 parts dried aluminum hydroxide gel to 20 parts glycerin) and then tray dried with hot air at 50° C. to an $Al_2O_3$ of 40%. The resulting dried cake was then pulverized to obtain a powdered product and a sample of this is called A.

The same wet gel as used for a starting material in Example 23 at 10% $Al_2O_3$ was tray dried with hot air at 50° C. to yield a dried gel at 50% $Al_2O_3$ and pulverized. 100 grams of the dried powder, 20 grams of glycerin and 100 grams of deionized water were needed and tray dried with hot air at 50° C. to an $Al_2O_3$ of 40% and pulverized and a sample of this is called B.

Samples A and B as above prepared were individually screened and portions below 44 microns in size were tested as follows:

10% suspensions of A and B were prepared by putting 4 grams of each powder and 36 ml deionized water into two separate 4" × 1" glass vials and hand shaking the capped vials 20 times to effect the suspensions. Stability is tabulated as follows:

| Product "A" | Suspension Age | | | | |
|---|---|---|---|---|---|
| | 5 min. | 10 min. | 15 min. | 30 min. | 60 min. |
| Suspension | 100.0% | 100.0% | 100.0% | 100.0% | 96.3% |
| Supernatant | 0.0% | 0.0% | 0.0% | 0.0% | 1.3% |
| Cake | 0.0% | 0.0% | 6.2% | 0.0% | 2.4% |

| Product "B" | Suspension Age | | | | |
|---|---|---|---|---|---|
| | 5 min. | 10 min. | 15 min. | 30 min. | 60 min. |
| Suspension | 93.8% | 75.2% | 75.2% | 44.1% | 43.2% |
| Supernatant | 0.0% | 12.4% | 12.4% | 38.3% | 34.6% |
| Cake | 6.2% | 12.4% | 12.4% | 17.6% | 22.2% |

While the foregoing description and examples exemplify specific ways in which our invention may be carried out it is understood that these are illustrative only and that the practice of the invention may take many and varied forms all within the spirit and scope of the invention and the appended claims.

What is claimed is:

1. An antacid composition prepared by drying a wet compressed aluminum hydroxide gel to solid form, which is capable of being readily resuspended to yield an opaque aqueous suspension which reflects the properties of the original compressed gel, comprising the codried combination of a hydrous gelatinous aluminum hydroxide material selected from the group consisting of (1) basic aluminum bicarbonate-carbonate, (2) basic aluminum bicarbonate-carbonate in combination with magnesium basic carbonate, magnesium hydroxide, or magnesium trisilicate, or mixtures thereof, and a water soluble food-grade di- or trihydroxy alcohol suitable for oral ingestion, wherein analysis of the dried product yields a figure in the range of from 30–60 percent by weight for the sum of aluminum hydroxide and magnesium hydroxide calculatd as $Al_2O_3$ and MgO and shows that there is also present at least 0.3 mol of carbonate calculated as $CO_2$ for each mol of $Al_2O_3$.

2. The antacid composition of claim 1, wherein said dried product contains in the range of about 5–50 percent by weight of said food-grade alcohol.

3. The antacid composition of claim 1, wherein the food-grade alcohol is propylene glycol.

4. The antacid composition of claim 1, wherein the food-grade alcohol is glycerin.

5. The antacid composition of claim 1, wherein the food-grade alcohol is 1,3 butylene glycol.

6. An antacid composition prepared by drying a wet compressed aluminum hydroxide gel to solid form, which is capable of being readily resuspended to yield an opaque aqueous suspension which reflects the properties of the original compressed gel, comprising, the codried combination of a compressed aluminum hydroxy bicarbonate-carbonate gel and a water soluble food-grade di- or trihydroxy alcohol suitable for oral ingestion, wherein the dried product contains from 40–50 percent $Al_2O_3$, from 20–30 percent food-grade alcohol and contains at least 0.3 mol of carbonate calculated as $CO_2$ for each mole of $Al_2O_3$.

7. A method for manufacturing an antacid composition in solid form comprising mixing from 1 to 25 parts by weight of a hydrous gelatinous aluminum hydroxide material with one part by weight of a water soluble di- or trihydroxy alcohol suitable for oral ingestion and drying the aqueous mixture to produce a dried product wherein the sum of aluminum hydroxide and any magnesium hydroxide present calculated as $Al_2O_3$ and MgO, is in the range of from 30-60 percent by weight and there is also present at least 0.3 mol of carbonate calculated as $CO_2$ for each mol of $Al_2O_3$, whereby said product is capable of being readily resuspended to yield an opaque aqueous suspension which reflects the properties of the original hydrous gelatinous aluminum hydroxide material.

8. The method of claim 7 wherein said hydrous, gelatinous aluminum hydroxide material is selected from the group consisting of basic aluminum bicarbonate-carbonate, magnesium basic carbonate, magnesium hydroxide, magnesium trisilicate, and mixtures thereof.

9. The method of claim 7 wherein said dried product contains in the range of about 15-35 percent by weight of said di- or trihydroxy alcohol.

10. The method of claim 7 wherein said alcohol is propylene glycol.

11. The method of claim 7 wherein said alcohol is glycerin.

12. The method of claim 7 wherein said alcohol is 1,3 butylene glycol.

13. The method of claim 7 wherein said aqueous mixture is dried by spray drying.

14. The method of claim 7 wherein said hydrous, gelatinous aluminum hydroxide material contains from 1 to 20 parts by weight of compressed aluminum hydroxide gel and from 1 to 5 parts by weight of water.

15. The method of claim 7 wherein said aqueous mixture is tray dried.

16. The method of claim 7 wherein said opaque mixture is dried in a drum drier.

17. An antacid composition prepared by drying a wet compressed aluminum hydroxide gel to solid form, which is capable of being readily resuspended to yield an opaque aqueous suspension which reflects the properties of the original gel, comprising the codried combination of a hydrous gelatinous aluminum hydroxide material selected from the group consisting of (1) basic aluminum bicarbonate-carbonate, (2) basic aluminum bicarbonate-carbonate in combination with magnesium basic carbonate, magnesium hydroxide, or magnesium trisilicate, or mixtures thereof, and polyethylene glycol having a molecular weight of from about 200 to 700, wherein analysis of the dried product yields a figure in the range of from 30-60 percent by weight for the sum of aluminum hydroxide and magnesium hydroxide calculated as $Al_2O_3$ and MgO and shows that there is also present at least 0.3 mol of carbonate calculated as $CO_2$ for each mol of $Al_2O_3$.

18. A method for manufacturing an antacid composition in solid form comprising mixing from 1 to 25 parts by weight of a hydrous gelatinous aluminum hydroxide material with one part by weight of polyethylene glycol having a molecular weight of from about 200 to 700 to produce a dried product wherein the sum of aluminum hydroxide and any magnesium hydroxide present calculated as $Al_2O_3$ and MgO, is in the range of from 30-60 percent by weight and there is also present at least 0.3 mol of carbonate calculated as $CO_2$ for each mol of $Al_2O_3$, whereby said product is capable of being readily resuspended to yield an opaque aqueous suspension which reflects the properties of the original hydrous gelatinous aluminum hydroxide material.

* * * * *